United States Patent [19] [11] 4,356,100
Sherman [45] Oct. 26, 1982

[54] SOFT CONTACT LENS COLD DISINFECTANT SOLUTION

[75] Inventor: Guy J. Sherman, Metairie, La.

[73] Assignee: Sherman Laboratories, Inc., Abita Springs, La.

[21] Appl. No.: 37,645

[22] Filed: May 10, 1979

[51] Int. Cl.³ .................. C11D 1/825; C11D 3/48
[52] U.S. Cl. .................. 252/106; 252/173; 252/174.17; 252/174.22; 252/546; 252/DIG. 14
[58] Field of Search ............. 252/106, 174.23, 174.24, 252/546, 174.17, DIG. 14, 173; 428/78, 80, 146; 134/40, 42

[56] References Cited

U.S. PATENT DOCUMENTS

| | | | |
|---|---|---|---|
| 3,329,607 | 7/1967 | Colobert et al. | |
| 3,911,107 | 10/1978 | Krezanoski | 428/78 |
| 3,987,163 | 10/1976 | Rankin | 428/78 |
| 4,013,576 | 3/1977 | Loshaek | 134/42 X |
| 4,046,706 | 9/1977 | Krezanoski | 134/42 X |
| 4,104,187 | 8/1978 | Sibley et al. | 134/40 X |
| 4,126,587 | 11/1978 | Sibley et al. | 134/42 X |
| 4,127,423 | 11/1978 | Rankin | 134/30 |
| 4,199,469 | 4/1980 | Walzer | 252/180 |

Primary Examiner—P. E. Willis, Jr.
Attorney, Agent, or Firm—Winburn & Gray, Ltd.

[57] ABSTRACT

An aqueous composition for cleaning rinsing and cold disinfecting of soft contact lenses during non-wearing periods is provided. The composition comprises a polyoxyethylene-polyoxypropylene block copolymer having a molecular weight between about 1,100 and 14,000, a water solubility in excess of about 10 grams per 100 milliliters, a cloud point in 1% aqueous solution above about 32° C. and a foam height in excess of 30 millimeters; a physiologically acceptable nonionic surface acting agent having a water solubility in excess of one gram per 100 milliliters, a cloud point in 1% aqueous solution of from about 65° C. to about 100° C. and a foam height in excess of 25 millimeters; a humectant, preservative, antimicrobial and fungal growth inhibitor composition which is physiologically compatible and compatible with soft and semi-hard contact lenses which includes ascorbic acid in a concentration of from about 0.1 percent to about 10.0 percent of the total aqueous composition.

8 Claims, No Drawings

SOFT CONTACT LENS COLD DISINFECTANT SOLUTION

BACKGROUND OF THE INVENTION

This invention relates to an effective rinsing, cold storage and disinfecting solution for the overnight or interim equilibration, disinfection, cleaning and storage of contact lenses. More particularly, this invention relates to a highly effective cold storage and disinfecting solution for the overnight or interim equalibration, disinfection, cleaning and storage of hydrophilic gel lenses, semi-hard contact lenses and gelflex material soft lenses including the following plastic gel materials: hydroxyethyl methacrylate (HEMA) or its analogues, ethylene glycol dimethacrylate (EGMA) or its analogues, polymethyl methacrylate (PMMA) or its analogues, the relatively new semi-hard contact lens material cellulose-acetate-butyrate (CAB) and silicone polymers.

In another aspect, this invention relates to the total patient regimen for maintaining and treating soft and semi-hard contact lenses.

Just as there are marked differences in the structure and composition of hard and soft contact lenses, there are also marked differences in the maintenance and care or treatment of the various types of hard, semi-hard and soft lenses. While patient care and treatment of hard contact or conventional contact lenses is relatively simple and uncomplicated, the proper care and treatment of the newer soft and hydrophilic lenses has proved to be more complex and time consuming.

The primary difference between the conventional hard contact lens and the more complex soft lenses is the marked increase in the polar or water attracting centers of the hydrophilic gel material. It is this property of the hydrophilic gel lens that gives the soft lens its own unique physical properties and clinical behaviour. This polar or water attracting center of the gel material is represented in the hydroxyethyl methacrylate bond as a hydroxyl group (-OH) which attracts and holds large amounts of water. It is this high water content held in the expanded matrix of the hydrophilic gel lens which leads to the special difficulties in cleaning and disinfecting or asepticising the soft hydrophilic lens. The hydrophilic nature of soft contact lenses makes the lenses vulnerable to bacterial contamination. While studies have demonstrated that bacteria cannot penetrate the actual intramolecular pores of the hydrophilic lens, except in defective lenses, the bacteria have an affinity for the protein and tear deposits on the surfaces of the lens matrix. In particular, the tears and fluids absorbed by the soft lenses serve as excellent bacterial culture media. If defects or nicks occur in the lens either during manufacture or subsequent patient wear, bacteria may find a haven to grow and be sheltered from superficial lens cleaning and disinfection.

Potentially harmful fungi also prove a possible danger to the soft contact lens. Fungi, like bacteria, can thrive in tear secretions or deposits and penetrate the lens material directly if enzymatic degradation of the lens material has taken place.

Similarly, any residual proteinaceous or tear secretion deposits remaining in or on the lens may readily inactivate the most effective germicidal components of a disinfecting system, and may thus serve to act as a growth media for a variety of potentially harmful microorganisms and fungi. It has been demonstrated in controlled laboratory duplication of actual lens wear situations and testing of resultant lens deposits that normally effective and suitable germicidal chemicals and agents can be largely inactivated or reduced in effectiveness by residual deposits on improperly cleaned lenses. While many germicidal and antiseptic agents in appropriate concentrations demonstrate the ability to disinfect fresh lenses, these same agents and antiseptics do not necessarily disinfect the lens when contaminating material is present on the lens surface. Therefore, an effective cleaning step or steps is an essential and mandatory part of any effective soft lens treatment and maintenance regimen. These cleaning steps can best be accomplished by using a specific lens cleaner as well as a rinsing, storage and disinfecting solution which incorporates a specific amount of each cleaning agent or agents. This will more readily insure that the disinfectant properties of the cold storage solution will not be overwhelmed by gross organic or inorganic deposits and pollutants.

Other problems can accrue from incorrect and careless handling of the soft lenses by the patient himself. Many potential contaminants and lens deposits can be transferred from unwashed fingers to the surface of the soft lens. These include oily deposits from the skin, sweat, skin lotions and creams, mascara, detergents, lipstick and even nicotine. Controlled studies have demonstrated that bacterial contaminants occur in 43% of the makeup used by women, and fungal contaminants in 12%. Attempts to effect sterilization of the lenses by boiling, for example, can be cumbersome in addition to causing permanent damage to the lenses if done improperly. If the patient has used impure water for storage and rinsing of the lenses, undesirable deposits such as calcium, iron and insoluble divalent and trivalent metallic salts as well as other chemical deposits can collect on the lens surfaces.

Therefore, a need has arisen for an effective composition to counteract and mitigate the above described effects of improper hygiene and lens handling as well as to provide optimum cleaning, rinsing, disinfection and equalibration of the soft lens between lens wearing periods. In addition, the active ingredients of the contact lens solution should: (1) disinfect clean soft lenses within a period of four to six hours and produce D values of a 90% kill rate of microorganisms, selected fungal organisms and viral agents such as herpes simplex; (2) not be easily inactivated by small amounts of proteins, lipids or other tear and extraneous components and deposits; (3) not bind to protein or other lens surface deposits from the eye; and (4) not react with or adsorb to the soft lens material or matrix. For example, several antiseptic agents which meet the above requirement for rapid and effective kill of a broad range of microorganisms have proved to be unsuitable for use in soft lens treatment solutions, in that these agents are incompatible with the soft lens material or bind with protein deposits on the surfaces of the lens matrix. Other antiseptic agents are unacceptable for use in soft lens solutions since they are concentrated by the lens material, to the extent that they cause discomfort and potential damage to the corneal surface of the wearer's eyes. Benzalkonium chloride is one such antiseptic agent which meets the requirements for effective and rapid killing of microorganisms but is unacceptable because it binds with many types of soft lens material and also binds with protein deposits on the lens surface.

One type of cold disinfecting solution for soft contact lenses uses chlorohexidine. However, chlorohexidine is absorbed by the soft contact lens material and gradually eluded into the eye often causing excessive burning, irritation and red eye, which can prevent the patient from wearing the lenses.

Therefore, a need has arisen for a highly effective cold storage and disinfecting solution for the overnight or interim equilibration, disinfection, cleaning and storage of soft and semi-hard contact lenses which meet the aforesaid requirements.

SUMMARY OF THE INVENTION

In accordance with the present invention, a highly effective cold storage and disinfecting solution containing ascorbic acid for the overnight or interim equilibration, disinfection, cleaning and storage of soft and semi-hard contact lenses within an optimum four hour period is provided. The aqueous composition in accordance with the invention effectively performs the aforesaid functions of lens care while at the same time maintains the integral structure and physical properties of the lens since the active ingredients of the formulation are fully compatible with and conducive to the physical and chemical components of the lens matrix or structure.

The aqueous composition in accordance with the invention comprises: from about 0.1% to about 8.6% by weight of the total aqueous composition of a polyoxypropylene-polyoxyethylene block copolymer having a molecular weight of about 1,100 to about 14,000, a water solubility in excess of 10 grams per 100 milliliters, a cloud point in one percent aqueous solution above about 32° C. and a foam height in excess of about 32 millimeters; from about 0.05% to about 0.45% by weight of the total aqueous composition of a physiologically acceptable nonionic surface acting agent having a water solubility in excess of 1 milliliter per 100 milliliters, a cloud point in one percent aqueous solution of from about 65° C. to about 100° C. and a foam height in excess of 25 millimeters; an effective amount of a humectant, preservative, antimicrobial and fungal growth inhibitor composition which is physiologically acceptable and compatible with the contact lenses, which composition includes ascorbic acid in a concentration of from about 0.1% to about 10.0% by weight of the total aqueous composition; propylene glycol in a concentration from about 0.2% to about 2.5% by weight of the total aqueous composition and a salt of ethylenediaminetetraacetic acid.

The remainder of the composition is purified water U.S.P. and may also include combinations of neutral and alkaline water soluble salts to provide an aqueous composition salt content equivalent to about 0.8% to about 1.8% sodium chloride by weight of the total aqueous composition. A polymeric viscosity building agent such as hydroxyethyl cellulose may optionally be included in the composition according to the invention, but is not intrinsic to the effectiveness of the invention.

In another embodiment of the invention, in a sterile aqueous formulation for storing, cleaning or disinfecting contact lenses comprising a surface active composition and a disinfectant composition, ascorbic acid comprises part of the formulation.

DETAILED DESCRIPTION OF THE INVENTION

One aspect of the invention relates to a cold storage and disinfecting aqueous solution for contact lenses which solution contains ascorbic acid in a precise blending of synergistic compounds including surface acting agents, preservatives, salts and antiseptics. Another aspect of the invention relates to a contact lens formulation for rinsing, storing, cleaning and disinfecting contact lenses which comprises a surface active composition, a disinfectant composition and ascorbic acid.

According to the invention, the aqueous contact lens solution includes a polyoxypropylene-polyoxyethylene block copolymer which is physiologically acceptable and compatible with soft and semi-hard contact lenses. The block copolymers for use in accordance with the invention have a molecular weight of about 1,100 to about 14,000, a water solubility in excess of 10 grams per 100 millimeters, a cloud point in 1% aqueous solution of about 32° C. and a foam height in excess of 32 millimeters.

As is well-known to those skilled in the art, the cloud point of a material is the temperature at which a soluble material becomes visible in solution as the aqueous solution containing the material is cooled or heated. As used herein, the foam height is the value obtained on a Dynamic Foam Tester operated at a temperature of 120° F. (49° C.) using a 0.1% polyol concentration at a flow rate of 400 milliliters per minute for 10 minutes.

One group of block copolymers suitable for use according to the invention are those sold by BASF Wyandott Corporation of Wyandotte, Michigan under the trade name "Pluronic." The following Pluronic block copolymers are suitable for use in accordance with the invention: Pluronic L-44, Pluronic L-62, Pluronic L-64, Pluronic F-68, Pluronic F-108 and Pluronic F-127.

The cold storage and disinfecting aqueous solutions according to the invention should contain from about 0.1% to about 8.6% by weight of the total aqueous composition of the block copolymer and preferably about 0.2% by weight of the total aqueous composition of the block copolymer.

The block copolymers are nonionic surface active agents serve to help remove ocular secretions and proteinaceous deposits which tenaciously cling to the soft lens surfaces and other deposits which include atmospheric contaminants, extraneous dirt, eye medications, makeup preparations such as mascara, and residual deposits on the soft lens that may occur from improper rinsing in impure tap water, for example.

To complement the cleansing characteristics of the block copolymers, the aqueous cleaning and disinfectant solution according to the invention also includes an alkylphenoxy polyethoxy ethanol octylphenol surface acting agent having a molecular weight of about 800, a water solubility in excess of one gram per 100 milliliters, a cloud point in one percent aqueous solution of from about 65° C. to about 100° C. and a foam height in excess of 25 millimeters. Preferably, the octylphenol surface acting agent is present in the aqueous cleaning and disinfecting solution of the invention in an amount of from about 0.05% to about 0.45% and preferably about 0.08% by weight of the total aqueous solution. The octylphenol surface acting agent helps to remove ocular secretions, proteinaceous deposits and other materials which may be deposited upon the surfaces of the lens.

Another surface acting agent that can be utilized in accordance with the present invention is polyoxyethylene sorbitan monolaurate having a molecular weight of from about 300 to about 4,000 and present in a concentration of from about 0.05% to about 0.4% by weight of the total aqueous composition.

The cleaning and disinfecting compositions of the present invention also include a combination of specific components combined together which act as a preservative, antibacterial and microbial and fungal growth inhibitor. The unique combination of preservatives, antibacterial, anti-microbial, and fungal growth inhibitors result in a well-balanced composition for use as a cold storage and disinfection solution.

The selection of appropriate antiseptic bactericidal and fungicidal chemical agents to complement the surface acting agents included in the composition requires that the selected chemical agents be physiologically acceptable at effective concentrations and be compatible with all other components of the solution as well as with the contact lens material. The essential considerations in determining the optimum antibacterial and antifungal agents are: (1) disinfects clean soft lenses within a period of four to six hours and produces D values of a 90% kill rate of microorganisms, selected fungal organisms and viral agents such as herpes simplex; (2) not easily inactivated by small amounts of proteins, lipids or other tear and extraneous components and deposits; (3) does not bind to protein or other lens surface deposits from the eye; and (4) does not react with or adsorb to the soft lens material or matrix.

According to the invention, the preferred combination of preservatives, antibacterial and antifungal compounds for use in the aqueous compositions of the present invention include: from about 0.2% to about 2.5% by weight of the total aqueous composition propylene glycol; an organic mercury disinfecting agent compatible with the contact lenses and present in a sufficient amount to insure preservation of the sterility of the aqueous composition and be physiologically acceptable; from about 0.1% to about 10.0% by weight of the total aqueous composition ascorbic acid; from about 0.5% to about 2.0% by weight of the total composition of a salt of ethylenediaminetetraacetic acid.

The preferred concentration of propylene glycol is about 0.70% by weight of the total aqueous composition. The propylene glycol acts as a humectant, preservative and fungal growth inhibitor.

The organic mercury disinfecting agent acts as a microbial and fungal growth inhibitor such as phenylmercuric acetate and Thimerosal. Thimerosal is the preferred organic mercury disinfecting agent according to the invention and should be present in amounts from about 0.001% to about 0.006%, with the preferred concentration being about 0.004% by weight of the total aqueous composition. While Thimerosal can be absorbed into soft contact lenses during heat sterilization if thimerosal is present during heat sterilization. However, during cold or ambient temperature storage, only very small quantities of thimerosal are absorbed by the lenses, without any apparent deleterious effects on the wearer.

Ascorbic acid is present in the composition according to the invention and present in amounts from about 0.1% to about 10.0% by weight of the total aqueous composition. The antiseptic properties of ascorbic acid are more effective against bacteria than fungal and viral organisms. When combined with thimerosal, ascorbic acid serves as a potentiating agent which enhances the effectiveness of the antiseptic system of the invention. In D value studies to demonstrate the log kill of microorganisms, ascorbic acid at concentrations of 1.0% to 5.0% was shown to produce a significant log kill of five selected microorganisms, including *Pseudomonas aeruginosa* and *Stephylococcus aureus* within a six hour time period. Ascorbic acid is found in all parts of the human body, including the blood stream and is found in greatest concentrations in the adrenal glands and the ocular tissue of the human body. Since ascorbic acid is a natural chemical and is nontoxic to ocular tissue in relatively large amounts and since its antibacterial properties increase with its concentration in solution, it is a safe and efficacious ingredient. The preferred concentration of ascorbic acid is about 8.0% by weight of said total composition. According to the invention, ascorbic acid can be present in a formulation for storing, cleaning or disinfecting contact lenses together with a disinfectant composition and a surface active composition. Thus, it is contemplated that disinfectant and surface active compositions other than disclosed herein may be used in conjunction with ascorbic acid.

In accordance with a more specific aspect of this general embodiment of the present invention, in a sterile aqueous formulation for storing, cleaning and disinfecting contact lenses that includes a surface active composition and a disinfectant composition, the formulation also includes ascorbic acid present in an amount of from about 0.1% to about 10.0% by weight of the total aqueous formulation.

The inclusion of a salt of ethylenediaminetetraacetic acid serves as a buffering and preservative component of the composition of this invention, maintaining the pH of the composition in an acid range, preferably between about 4.0 and about 7.0, and has also been demonstrated to have antibacterial and antifungal properties. The preferred salt of ethylenediaminetetraacetic acid is disodium ethylenediaminetetraacetate and present in a concentration of from about 0.5% to about 2.0% by weight of the total aqueous composition.

Optionally, the aqueous composition according to the invention may also include a polymeric viscosity building agent such as hydroxyethyl cellulose. The polymeric viscosity building agent is not intrinsic to the effectiveness of the composition.

The remainder of the composition is purified water U.S.P. and preferably includes combinations of essentially neutral and alkaline salts compatible with ocular tissue which are water soluble and present in a concentration to provide an aqueous composition salt content equivalent to from about 0.8% to about 1.8% sodium chloride by weight of the total aqueous composition. Thus, the preferred compositions according to the invention include a combination of salts compatible with ocular tissue present in a concentration having a tonicity which is about the same as or slightly higher than the tonicity of normal human tear fluid. Mildly hypertonic solutions can be desirable since the solution will have a greater osmotic pressure than that of the tear fluid of the contact lens wearer. Neutral water soluble salts which can be used in the aqueous composition of the invention include salts such as sodium chloride and potassium chloride. Alkaline water soluble salts which can be used in accordance with the invention include salts such as sodium bicarbonate. Preferably sodium chloride and potassium chloride are combined together in a weight ratio of from about 2:1 to 7:3, respectively.

The aqueous composition according to the invention is preferably utilized as part of the total patient regimen for maintaining and treating soft and semi-hard lenses. Thus, an effective cleaning step or steps is an important part of any effective soft or semi-hard lens treatment and maintenance regimen. Separate cleaning of the lenses insures that the disinfectant properties of the aqueous solution according to the invention will not be overwhelmed by gross organic or inorganic deposits and pollutants.

Whereas the present invention has been described with respect to specific embodiments thereof, it will be understood that various changes and modifications will be suggested to one skilled in the art and it is intended that the invention encompass such changes and modifications as fall within the scope of the appended claims.

I claim:

1. A sterile, aqueous composition consisting essentially of water, from about 0.1% to about 8.6% by weight of said total aqueous composition of a polyoxypropylene-polyoxyethylene block copolymer having a molecular weight of about 1,100 to about 14,000, a water solubility in excess of about 10 grams per 100 milliliters, a cloud point in 1% aqueous solution above about 32° C. and a foam height in excess of about 32 millimeters, from about 0.05% to about 0.45% by weight of said total aqueous composition of an alkylphenoxy polyethoxy ethanol octylphenol that is a physiologically acceptable non-ionic surface acting agent having a water solubility in excess of about 1 milliliter per 100 milliliters, a cloud point in 1% aqueous solution of from about 65° C. to about 100° C. and a foam height in excess of about 25 millimeters, from about 0.1% to about 10% ascorbic acid by weight of the total aqueous composition, from about 0.001% to about 0.006% Thimerosal by weight of the total aqueous composition, from about 0.2% to about 2.5% propylene glycol by weight of the total aqueous composition, a salt of ethylenediaminetetraacetic acid suitable for use as a preservative and buffer and present in an amount to maintain the pH of the aqueous composition in a range of between about 4.0 and 7.0, which composition disinfects soft and semi-hard contact lenses within four hours, is compatible with soft and semi-hard lenses to allow storage therein and is suitable for cleaning soft and semi-hard contact lenses.

2. The aqueous composition as recited in claim 1 further consisting essentially of a sufficient amount of water soluble salts compatible with ocular tissue and present in a concentration sufficient to provide a solution salt content equivalent to about 0.8% to about 1.8% sodium chloride by weight of the total aqueous composition.

3. The aqueous composition as recited in claim 2 wherein two essentially neutral water soluble salts are present in the aqueous composition.

4. The aqueous composition as recited in claim 3 wherein said essentially neutral salts are sodium chloride and potassium chloride.

5. The aqueous composition as recited in claim 1 wherein said surface acting agent is an alkylphenoxy polyethoxy ethanol octylphenol surface acting agent having a molecular weight of about 800.

6. The aqueous composition as recited in claim 1 wherein said salt of ethylenediaminetetraacetic acid is disodium ethylenediaminetetraacetate present in a concentration of from about 0.5% to about 2.0% by weight of said total composition.

7. The aqueous composition as recited in claim 1 further consisting essentially of a hydroxyethyl cellulose viscosity building agent.

8. The composition as recited in claim 1 wherein ascorbic acid is present in the aqueous composition in an amount of about 8.0% by weight of the total aqueous composition.

* * * * *